United States Patent
Ashmore et al.

(10) Patent No.: US 10,143,195 B2
(45) Date of Patent: Dec. 4, 2018

(54) STABLE BIOCIDE COMPOSITIONS

(75) Inventors: John William Ashmore, Lansdale, PA (US); Boris Polanuyer, Lansdale, PA (US)

(73) Assignee: ROHM AND HAAS COMPANY, Collegeville, PA (US)

( * ) Notice: Subject to any disclaimer, the term of this patent is extended or adjusted under 35 U.S.C. 154(b) by 406 days.

(21) Appl. No.: 13/490,588

(22) Filed: Jun. 7, 2012

(65) Prior Publication Data
US 2012/0315400 A1 Dec. 13, 2012

Related U.S. Application Data

(60) Provisional application No. 61/494,078, filed on Jun. 7, 2011.

(51) Int. Cl.
| *C09D 5/14* | (2006.01) |
| *B05D 3/00* | (2006.01) |
| *A01N 25/04* | (2006.01) |
| *A01N 43/80* | (2006.01) |

(52) U.S. Cl.
CPC ............. *A01N 25/04* (2013.01); *A01N 43/80* (2013.01); *C09D 5/14* (2013.01)

(58) Field of Classification Search
CPC ........ A01N 25/04; A01N 25/26; A01N 25/28; A01N 25/30; A01N 43/80; A01N 47/14; A01N 23/00; A01N 2300/00; C09D 5/14

USPC ........ 523/122; 514/941; 427/385.5; 524/198
See application file for complete search history.

(56) References Cited

U.S. PATENT DOCUMENTS

| 5,273,953 | A | | 12/1993 | Szekely et al. |
| 5,444,078 | A | * | 8/1995 | Yu ........................... A01N 25/02 |
| | | | | 210/749 |
| 5,827,522 | A | * | 10/1998 | Nowak .......................... 424/405 |
| 7,377,968 | B2 | | 5/2008 | Reybuck et al. |
| 2007/0053950 | A1 | | 3/2007 | Gajanan et al. |
| 2007/0202139 | A1 | | 8/2007 | Bigorra Llosas et al. |
| 2007/0215000 | A1 | | 9/2007 | Reybuck et al. |
| 2012/0164203 | A1 | | 6/2012 | Premachandran et al. |

FOREIGN PATENT DOCUMENTS

EP 475781 A1 * 3/1992

* cited by examiner

*Primary Examiner* — Josephine L Chang
(74) *Attorney, Agent, or Firm* — Tifani M. Edwards

(57) ABSTRACT

Provided is a solvent borne coating composition comprising (a) one or more polymeric biocide comprising multivalent metal cations and multivalent organic anions, (b) one or more polymer-encapsulated biocide, and (c) one or more ethoxylated triglyceride that has average number of moles of ethylene oxide units per mole of triglyceride molecules of 10 to 45. Also provided are a method of making such composition and a method of using such a composition.

4 Claims, No Drawings

STABLE BIOCIDE COMPOSITIONS

It is often desired to prepare solvent borne antifouling coating compositions that contain more than one biocide. Specifically, it is often desired to prepare such a composition in which one of the biocides is in the form of particles that are encapsulated by a polymer and another biocide is a polymeric complex of multivalent metal cations and multivalent organic anions. In such cases, the two biocides are often incompatible, which causes the coating composition to be unstable, leading to agglomeration of particles or other symptoms of instability.

U.S. Pat. No. 7,377,968 describes coating compositions that contain microencapsulated DCOIT (4,5-dichloro2-n-octyl-3(2H)-isothiazolone and also contain free DCOIT.

It is desired to provide a solvent borne antifouling coating composition that is resistant to agglomeration of particles and that contains a first biocide in the form of particles that are encapsulated by a polymer and a second biocide in the form of a polymeric complex of multivalent metal cations and multivalent organic anions.

The following is a statement of the invention.

A first aspect of the present invention is a solvent borne coating composition comprising (a) one or more polymeric biocide comprising multivalent metal cations and multivalent organic anions, (b) one or more polymer-encapsulated biocide, and (c) one or more ethoxylated triglyceride that has average number of moles of ethylene oxide units per mole of triglyceride molecules of 10 to 45.

A second aspect of the present invention is a method of making the composition described in the first aspect. A third aspect of the present invention is a method of using the composition described in the first aspect.

The following is a detailed description of the invention.

As used herein, the following terms have the designated definitions, unless the context clearly indicates otherwise.

A biocide is a compound that is capable of inhibiting the growth of, or killing, one or more species of bacteria, fungus, algae, or marine fouling organisms. Marine fouling organisms tend to grow on surfaces that are submerged under water and include hard and soft fouling organisms, including algae, tunicates, hydroids, bivalves, bryozoans, polychaete worms, sponges, and barnacles.

A coating composition is a composition that is capable of being applied as a layer on the surface of a substrate and capable of forming a dry layer (the "dry coating") that adheres to the surface of the substrate.

A marine coating composition is a coating composition that is capable of forming a dry coating on the surface of a marine object. After formation of the dry coating, the dry coating will adhere to the surface for a usefully long time, even when some or all of the coated surface remains under water for significant amounts of time (i.e., at least one hour per day). Marine objects are those that are put to use in environments in which some or all of the object is under water for significant amounts of time. Examples of marine objects include ships, piers, docks, pilings, fishnets, heat exchangers, dams, and piping structures, such as intake screens.

A marine coating composition that is effective at inhibiting the growth of one or more marine fouling organism is a marine anti-fouling (MAF) coating composition. A marine anti-foulant is a compound that is added to a marine coating composition and that improves the ability of the marine coating composition to inhibit the growth of one or more marine fouling organism. A marine anti-foulant that improves the ability of the marine coating composition to inhibit the growth of soft fouling organisms is a "co-biocide." A marine anti-foulant that improves the ability of the marine coating composition to inhibit the growth of hard fouling organisms is a "main biocide."

A liquid composition is in the liquid state in a standard atmosphere over a temperature range that includes 0° C. to 60° C. A solvent borne composition is a liquid composition that has a continuous liquid medium, and the continuous liquid medium contains one or more compound that is not water. The continuous liquid medium of a solvent borne composition contains 0% to 10% water, by weight based on the weight of the continuous liquid medium.

A polymer (synonymously called a polymeric compound) is a relatively large molecule made up of the reaction products of smaller chemical repeat units. A polymer has number-average molecular weight of 1,000 or higher. Polymers may be homopolymers in which the repeat units are all identical or copolymers in which two or more different repeat units are present.

A fatty acid is a compound that contains at least one linear chain of 8 or more carbon atoms and that contains a carboxylic group. A triglyceride is a compound that has the structure that would result if three fatty acids formed ester links to the three hydroxyl groups on a single molecule of glycerol. Each of the three fatty acid portions of the triglyceride is called a "residue" of the fatty acid. Some fatty acid residues contain one or more hydroxyl group attached to one or more of the carbon atoms.

An ethylene oxide unit is the bifunctional radical $-(CH_2-CH_2-)$. An ethoxylated compound has the structure $R-O-(CH_2-CH_2O-)_n H$, where n is 1 or higher, and R is any organic radical. R may or may not contain or be attached to additional ethylene oxide units.

An organic compound or radical is a compound or radical that contains one or more carbon atom. The category "organic compound or radical" excludes the following: binary compounds of carbon such as carbon dioxide and carbon disulfide; ternary compounds of carbon such as metallic cyanides, metal carbonyls, phosgene, and carbonyl sulfide; and metal carbonates.

A multivalent cation is a cation with a positive charge equivalent to two or more protons. A multivalent anion is an anion with a negative charge equivalent to two or more electrons.

As used herein, the term "final paint" describes a composition of the present invention that is completed and is therefore suitable to be put to use as a coating When the phrase "most of" a certain substance is used herein, it is meant 50% or more of that substance, based on the total amount of that substance that is present in the final paint.

Nonionic surfactants are surface-active compounds that are not ionized when dissolved in water at 25° C. at any pH between 5 and 9. Nonionic surfactants have a portion of the molecule that is hydrophobic and a portion of the molecule that is hydrophilic. Nonionic surfactants each have an "HLB" (Hydrophilic/Lipophilic Balance) number. The HLB number for a surfactant is often available from the manufacturer of the surfactant, and many HLB values are tabulated in publications such as, for example, *McCutcheon's Detergents and Emulsifiers*, published annually by MC Publishing Company, Princeton, Wis. 54968 USA.

As used herein, the term "xylene" refers to any isomer or mixture of isomers of dimethylbenzene. Usually, xylene is a mixture of all three isomers: 1,2-dimethylbenzene, 1,3-dimethylbenzene, and 1,4-dimethylbenzene.

The composition of the present invention is a solvent borne coating composition. The preferred amount of water in the continuous liquid medium is, by weight based on the weight of the continuous liquid medium, 10% or less; more preferably 5% or less; more preferably 2% or less; more preferably 1% or less.

Preferred continuous media contain one or more solvent selected from aliphatic compounds (such as mineral spirits), aromatic compounds, alkyl-substituted aromatic compounds (such as xylene, Solveso solvents, and Aromatic 100 and Aromatic 150 solvents), ketones (such as methyl isobutyl ketone and methyl isoamyl ketone), alcohols (such as n-butanol and propylene glycol methyl ethers), and mixtures thereof. Preferred are alkyl-substituted aromatic compounds and mixtures of alkyl-substituted aromatic compounds with ketones; more preferred are xylene and mixtures of xylene with methyl isobutyl ketone.

The composition of the present invention contains one or more polymeric biocide (a) comprising multivalent metal cations and multivalent organic anions. As the metal portion of the multivalent metal cations, preferred metals are alkaline earth and transition metals; more preferred are transition metals; more preferred are transition metals from row 4 of the periodic table; more preferred are zinc and manganese; more preferred is zinc. A mixture of two or more different metals may be used. Preferred metal cations have charge of +2.

Preferred multivalent organic anions have two or more separated anionic groups. Preferably the two or more anionic groups each have charge of −1. Preferred are compounds in which the anionic groups are separated by a chain of atoms that includes at least two methylene groups. That is, preferred multivalent organic anions have the structure

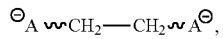

where $A^{\ominus}$ represents any anionic group, and the wavy curves represent that $A^{\ominus}$ may be bonded directly to $CH_2$ or there may be one or more atoms in between. A preferred anionic group is the dithiocarbamate ion, which has the structure

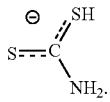

A preferred multivalent organic anion is ethylenebisdithiocarbamate ion, which has the structure

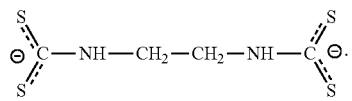

The biocide (a) of the present invention is polymeric. Among polymeric biocides that have divalent metal ions (i.e., metal ions of charge +2) and multivalent anions of the structure

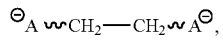

it is contemplated that the polymeric biocide has the structure

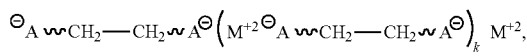

where k is 2 or greater, and where $M^{+2}$ represents a divalent metal ion; it is contemplated that, in the structure shown for the polymeric biocide, the anion at the left end may come into proximity with the cation on the right end to form a cyclic structure.

Preferably, the amount of polymeric biocide (a) is, by weight based on the weight of the composition of the present invention, 0.3% or more; preferably 1% or more; more preferably 3% or more. Preferably, the amount of polymeric biocide (a) is, by weight based on the weight of the composition of the present invention, 10% or less; more preferably 8% or less; more preferably 6% or less.

The biocide portion of the polymer encapsulated biocide (b) preferably has the following characteristics. Preferred biocides have solubility in water at 25° C., by weight based on the weight of the water, of 2% or less; more preferably 1% or less. Preferred biocides are isothazolones; more preferred are 4,5-dichloro-2-n-octyl-3(2H)-isothiazolone (DCOIT), 2-n-octyl-3(2H)-isothiazolone (OIT), benzisothiazolone (BIT), alkyl derivatives thereof, and mixtures thereof; more preferred are DCOIT, OIT, BIT, and mixtures thereof; more preferred is DCOIT.

The biocide inside the encapsulating polymer shell may be mixed with a partially water-miscible solvent, which is a solvent that has solubility in water at 25° C. of 0.01% to 5% by weight based on the weight of the water. If such a solvent is present, preferred are solvents having boiling point at 1 atmosphere pressure of 100° C. or higher.

The polymer portion of the polymer encapsulated biocide (b) has the following characteristics. Preferred polymers are impermeable to the solvent used in the composition of the present invention and have a useful degree of permeability to water. Preferred polymers are aldehyde-based condensation resins and blends of a hydrophilic dopant with an aldehyde-based condensation resin. When a dopant is used, preferred dopants are partially and fully hydrolyzed polyvinyl alcohol (PVOH), hydroxyethyl cellulose, hydroxypropylcellulose, methyl cellulose, hydroxyethylmethylcellulose, hydroxypropylmethylcellulose, hydroxybutylmethylcellulose, ethylhydroxyethylcellulose, polyethylene glycols, and mixtures thereof. When a dopant is used, more preferred dopant is partially or fully hydrolyzed PVOH.

Aldehyde-based condensation resins are reaction products of an aldehyde with one or more aldehyde-reactive compound. Preferred aldehydes are formaldehyde, glutaraldehyde, and mixtures thereof. Preferred aldehyde-reactive compounds are amines, amides, ureas, phenols, and mixtures thereof. A phenol is a compound in which one or more hydroxyl group is bonded to a carbon atom that is part of an aromatic ring; phenols may or may not have further substituents attached to the aromatic ring. More preferred aldehyde-reactive compounds are melamine, urea, resorcinol, and mixtures thereof. Preferred aldehyde-based condensation resins are urea-formaldehyde resins, melamine-formaldehyde resins, melamine-urea-formaldehyde resins, urea-resorcinol-glutaraldehyde resins, urea-resourcinol-formaldehyde resins, and cationic urea resins. Cationic urea resins are aldehyde-based condensation resins that are made with urea (and possibly with one or more additional aldehyde-reactive compound) and that are reacted, after the resin is formed, with one or more reagent to create cationic groups covalently attached to the resin.

In some embodiments, the polymer encapsulated biocide is first encapsulated in an acrylic polymer, and the resulting moiety is then encapsulated in a blend of a hydrophilic dopant and an aldehyde-based condensation resin.

If a particle of the polymer encapsulated biocide is not spherical, that particle's diameter is considered herein to be the diameter of a sphere that has the same volume as that particle. The particles of polymer encapsulated biocide preferably have weight-average diameter of 100 nanometers or higher. The particles of polymer encapsulated biocide preferably have weight-average diameter of 100 micrometer or lower; more preferably 50 micrometer or lower.

The amount of polymer encapsulated biocide (b) is characterized by the active weight percent, which is the weight of actual biocide (which does not include the weight of the encapsulating polymer) divided by the weight of the composition of the present invention, expressed as a percentage. The preferred active weight percent of polymer encapsulated biocide (b) is 0.1% or more; more preferably 0.3% or more; more preferably 1% or more. The preferred active weight percent of polymer encapsulated biocide (b) is 10% or less; more preferably 7% or less; more preferably 5% or less.

It is contemplated that in some embodiments, some DCOIT is present in the composition of the present invention in encapsulated form and further DCOIT is present in non-encapsulated form (i.e., dissolved in the solvent). In such embodiments, the total weight percent of DCOIT in the composition of the present invention is considered to be the sum of the active weight percent of the encapsulated DCOIT plus the ordinary weight percent of the non-encapsulated DCOIT (i.e., the weight of non-encapsulated DCOIT expressed as a percentage of the weight of the composition of the present invention).

The composition of the present invention contains one or more ethoxylated triglyceride. Preferred ethoxylated triglycerides are reaction products of one or more naturally-occurring triglyceride with ethylene oxide. Preferred naturally-occurring triglycerides have one or more hydroxyl group attached to one or more carbon atom in one or more of the residues of fatty acid. More preferred is castor oil.

A useful way to characterize ethoxylated triglycerides is NEO, which is the average number of moles of ethylene oxide units per mole of triglyceride molecules. Preferably NEO is 5 or higher; more preferably 10 or higher. Preferably NEO is 55 or lower; more preferably 45 or lower.

The preferred amount of ethoxylated triglyceride is, by weight based on the weight of the composition of the present invention, 0.05% or more; more preferably 0.1 or more; more preferably 0.2% or more; more preferably 0.4% or more. The preferred amount of ethoxylated triglyceride is, by weight based on the weight of the composition of the present invention, 5% or less; more preferably 2% or less; more preferably 1% or less; more preferably 0.75% or less.

Preferred ethoxylated triglycerides are nonionic surfactants. Preferred ethoxylated triglycerides have HLB value from 7 to 15.

Preferably, polymeric biocide (a) and polymer encapsulated biocide (b) are both co-biocides.

If a co-biocide other than polymeric biocide (a) and polymer encapsulated biocide (b) is present, the co-biocide other than polymeric biocide (a) and polymer encapsulated biocide (b) is preferably chosen from the group consisting of zinc pyrithione, copper pyrithione, tolyl fluinid, dichlo fluinid, diiodomethyl-p-tolylsulfone (DIMTS), 2-methylthio-4-tert-butylamino-6-isopropylamino-s-triazine, dichlorophenyl dimethyl urea, Zinc,bis(N,N-dimethylcarbamodithioato-kS,kS')[m-[[N,N'-1,2-ethanediylbis [carbamodithioato-kS, kS']](2-)]]di-(TOC 3204F), non-encapsulated DCOIT, and mixtures thereof.

Preferably, the composition of the present invention contains one or more main biocide. Preferred main biocides are selected from the group consisting of cuprous oxide, cuprous thiocyanate, excess DCOIT, spinosad, spinetoram, medetomidine, cypermethrin, tralopyr, TPBP, and mixtures thereof. By "excess DCOIT" it is meant any amount of DCOIT that is present in the composition of the present invention beyond a total weight percent of DCOIT of 3%. For example, if the total weight percent of DCOIT in a composition of the present invention were 7%, it would be considered herein that the co-biocide portion of the composition included DCOIT in the amount of 3 weight percent and that the main biocide portion of the composition included DCOIT in the amount of 4 weight percent.

Preferably the composition of the present invention contains one or more binder. A binder is a substance that is capable of forming a film; that is, when the binder is present in a solvent borne composition, when that composition is applied as a layer on a substrate and then dried or allowed to dry at ambient temperature (which may be any temperature from 0° C. to 45° C.) to form a dry coating, the binder is capable of forming a continuous film in that dry coating. During and after the drying process, the binder may or may not undergo chemical reactions that increase molecular weight and/or create crosslinks; if such chemical reactions occur, it is contemplated that the chemical reactions will not prevent the binder from forming a film. Preferred binders are soluble in the continuous liquid medium of the composition. Preferred binders contain one or more rosin, one or more polymer, or a mixture thereof. Preferred rosins includes unmodified rosin and alkylated rosin esters. Preferred polymers include acrylic resin acid salts; more preferred are zinc and copper salts of acrylic resin acids.

When one or more binder is present, the preferred total amount of all binder is, by weight based on the total weight of the composition, 5% or more; more preferably 10% or more. When one or more binder is present, the preferred total amount of all binder is, by weight based on the total weight of the composition, 30% or less; more preferably 25% or less.

Preferably the composition of the present invention further contains one or more pigment. A pigment is a particulate solid. A pigment is solid over a temperature range that includes the range −10° C. to 95° C. A pigment is present in the form of particles, which may be spherical, approximately spherical, irregularly rounded, roughly rectangular, sheet-like, lamelliform, needlelike, bristlelike, threadlike, or a combination thereof. A pigment may be organic (for example, polymeric) or inorganic (for example, oxides, carbonates, clays, etc.). When a particle is not spherical, its diameter is considered herein to be the diameter of a sphere that has the same volume as that particle.

When pigment particles are present in the composition of the present invention, the preferred weight-average diameter of the particles is 0.2 micrometers to 10 micrometers.

When one or more pigment is present, the preferred total amount of pigment is, by weight based on the total weight of the composition, 20% or more; more preferably 40% or more. When one or more pigment is present, the preferred total amount of pigment is, by weight based on the total weight of the composition, 75% or less; more preferably 65% or less.

The coating composition of the present invention optionally further contains one or more adjuvant. Some adjuvants include, for example, dispersants, coalescents, thickeners, colorants, waxes, additional biocides, and mixtures thereof. Preferred are compositions that contain adjuvants that are suitable for use in marine anti-fouling paints.

In the practice of the present invention, it is preferred to mix most or all of the solvent with most or all of the one or more ethoxylated triglyceride, prior to mixing solvent with polymer encapsulated biocide and prior to mixing solvent with polymeric biocide.

In describing the preferred methods of making the composition of the present invention, it is useful herein to label as "primary ingredients" the following: every polymer-encapsulated biocide, every polymeric biocide, and every ethoxylated triglyceride. All other ingredients present in the solvent borne coating composition of the present inventions are herein labeled "secondary ingredients."

In the following description, some processes are labeled as "first step," "second step," etc. It is contemplated that these steps will be performed in the order specified by the labels "first," "second," etc. It is further contemplated that other steps may be performed before, during or after the labeled steps, unless the descriptions state otherwise.

A preferred first step in making the composition of the present invention is to make a "base paint." As used herein, a base paint is a mixture that contains most or all of all the secondary ingredients and that contains little or none of the primary ingredients. By "little or none of the primary ingredients" it is mean that the total weight of primary ingredients in the base paint is 5% or less (by weight based on the total weight of all the primary ingredients that will be present in the final paint). More preferably, the amount of all the secondary ingredients in the base paint, by weight based on the weight of all secondary ingredients that will be present in the final paint, is 75% or more; more preferably 90% or more; more preferably 95% or more. More preferably, the amount of primary ingredients in the base paint, by weight based on the weight of all primary ingredients that will be present in the final paint, is 1% or less; more preferably 0.1% or less; more preferably 0%. It is preferred that the base paint be stirred, shaken, ground, milled, or otherwise agitated to thoroughly mix all the ingredients therein.

A preferred second step in making the composition of the present invention is to add most or all of the one or more ethoxylated triglyceride to the base paint to form a secondary mixture. More preferably, the amount of all the ethoxylated triglycerides in the secondary mixture is, by weight based on the weight of all ethoxylated triglycerides that will be present in the final paint, is 75% or more; more preferably 90% or more; more preferably 95% or more; more preferably 100%. It is preferred that the secondary mixture be stirred, shaken, or otherwise agitated to thoroughly mix all the ingredients therein. At the completion of the second step, it is preferred that the ethoxylated triglyceride is well distributed throughout the secondary mixture.

A preferred third step in making the composition of the present invention is to add most or all of the one or more polymer-encapsulated biocide and most or all of the one or more polymeric biocide to the secondary mixture to make a final paint. It is contemplated that the one or more polymer-encapsulated biocide and the one or more polymeric biocide may be added in any order, may be added simultaneously, may be added as a mixture, or any combination thereof. It is preferred that the final paint be stirred, shaken, or otherwise agitated to thoroughly mix all the ingredients therein.

For example, some embodiments that employ the preferred first step, preferred second step, and preferred third step described herein above are performed as follows. A base paint is made using all of the secondary ingredients except that the amount of solvent in the base paint is somewhat less than desirable in the final paint; such a base paint is often called "high solids." The preferred second step and preferred third step described above are performed, and then additional solvent is added.

Preferably, if any adjuvants are used, they are added to the base paint prior to the preferred second step described herein above.

The final paint is the composition of the present invention and is preferably put to use without further additions.

The composition of the present invention is preferably used as a coating; more preferably as an anti-fouling coating; more preferably as a marine anti-fouling coating.

When the composition of the present invention is put to use as a coating, a layer of the composition is applied to a substrate. The thickness of the layer is preferably chosen so that the dry film thickness will be 50 micrometers or more; more preferably 100 micrometers or more. The thickness of the layer is preferably chosen so that the dry film thickness will be 1 millimeter or less; more preferably 500 micrometers or less; more preferably 300 micrometers or less.

The following are examples of the present invention.

The following nonionic surfactants were tested:

| Name | Description | Source | HLB |
|---|---|---|---|
| Ethox ™ CO-5 surfactant | Ethoxylated Castor Oil, NE = 5 EO | (1) | (3) |
| Ethox ™ CO-16 surfactant | Ethoxylated Castor Oil, NE = 16 EO | (1) | 8.6 |
| Ethox ™ CO-40 surfactant | Ethoxylated Castor Oil, NE = 40 EO | (1) | 13 |
| Alkaterge ™ E surfactant | Ethyl Hydroxymethyl Oleyl Oxazoline | (2) | (3) |
| Flexitane ™ CA 6000 surfactant | Nitroparaffin | (2) | (3) |
| Tergitol ™ 15-S-5 surfactant | Secondary Alcohol Ethoxylate | (2) | 10.5 |
| Tergitol ™ 15-S-20 surfactant | Secondary Alcohol Ethoxylate | (2) | 17.4 |

Note (1): Ethox Chemicals LLC
Note (2): The Dow Chemical Company
Note (3): HLB is unknown The following materials were also used:

| Abbr. | Name | Description | Source |
|---|---|---|---|
| Base | Micron ™ 66 paint | commercially available MAF paint | AKZO |
| CR | SeaNine ™ CR Marine Anti-Fouling Agent | polymer encapsulated DCOIT | Dow Chemical Co. |
| CPT | Copper pyrithione | commodity | |
| ZINEB | Zinc ethylenebis-dithiocarbamate | commodity | |

Coating compositions were made using the following "standard" method.

Base was shaken using Red Devil™ paint mixer for 1-2 min. 40 g of paint was put into in 100 ml plastic bottle. Anionic surfactant was put into the bottle with the paint. The bottle was closed and then heated at 50° C. for 15 min. The bottle was then agitated using Red Devil paint mixer for 15 min. ZINEB was added into the bottle. The bottle was closed and then heated at 50° C. for 15 min. The bottle was then agitated using Red Devil paint mixer for 15 min. CR was added into the paint. The bottle was closed and then heated at 50° C. for 15 min. The bottle was then agitated using Red Devil paint mixer for 15 min.

The size of the dispersed particles in the composition were assessed with a Hegman gauge. A Hegman gauge is a block with a series of grooves that each becomes progressively more shallow along its length. Wet coating composition is pooled at the deep end of the grooves, and the coating composition is spread over the grooves with a scraper. The surface of the wet coating composition is observed, and the locations where the wet coating composition surface is uneven are noted. The depth of the groove at the deepest point at which unevenness is observed is taken as the size of the largest dispersed particles. That depth is reported as the particle size of the dispersed particles.

Coating compositions were made as described above and were then evaluated using the Hegman gauge.

EXAMPLE 1

Comparison of Various Anionic Surfactants

Coating compositions were made as described above, using the following weight percents based on the total weight of the coating composition: 1% nonionic surfactant, 5% ZINEB, and 2% CR. Each coating composition was analyzed with the Hegman apparatus.

The results were as follows. Examples with "C" in the Example Number are comparative examples.

| Example Number | Nonionic Surfactant | HLB | Hegman (micrometers) |
|---|---|---|---|
| 1-1 | Ethox CO-16 | 8.6 | 35 |
| 1-2 | Ethox CO-40 | 13 | 35 |
| 1-C3 | Tergitol 15-S-5 | 10.5 | >60 |
| 1-C4 | Tergitol 15-S-20 | 17.4 | >50 |
| 1-C5 | none | | >90 |

The samples without Ethox all showed unacceptable growth of the size of dispersed particles, showing that the formulations without Ethox were unstable. The sample with Tergitol 15-S-5 showed instability, even though it has HLB that is in between the HLB values of the two successful Ethox samples.

EXAMPLE 2

Order of Addition

Coating compositions 2-C1 and 2-2 were made as described above using 40 g of Base, 0.2 g of Ethox CO-16, 2 g of ZINEB, and 0.8 g of CR.

For Comparative Example 2-C1, these four ingredients were mixed together by hand in a container in the order Base, then Ethox CO-16, then ZINEB, then CR. Then the mixture was heated at 50° C. for 15 min, and then the mixture was placed on the high-speed orbital shaker at 780 rpm for 15 min.

Example 2-2 was made using the "standard" method defined above.

Comparative Example 2-C1 and Example 2-2 were analyzed with the Hegman apparatus. Comparative Example 2-C1 showed 55 micrometers, while Example 2-2 showed 35 micrometers. This result shows that Comparative Example 2-C1 leads to instability and agglomeration of particles, while Example 2-2 does not. That is, simultaneous addition of the ingredients leads to instability, while the "standard" method does not.

EXAMPLE 3

Non-Polymeric Biocide

A coating composition labeled Example 3-C1 was made using the standard method defined above except that zinc pyrithione, which is not polymeric, was used instead of zinc ethylenebisdithiocarbamate, which is considered to be polymeric. No evidence of instability was observed with Example 3-C1.

EXAMPLE 4

A coating composition labeled Example 4-C1 was made using the standard method defined above, using Ethox CO-5. Increase of particle size was observed in 4-C1.

The invention claimed is:

1. A stable solvent borne coating composition comprising
  (a) one or more polymeric biocide comprising zinc ethylenebisdithiocarbamate
  (b) one or more polymer-encapsulated biocide, wherein the biocide portion of said polymer-encapsulated biocide is 4,5-dichloro-2-n-octyl-3(2H)-isothiazolone; and
  (c) one or more solvent mixed with an ethoxylated triglyceride apart from the biocides wherein said ethoxylated triglyceride is an ethoxylated castor oil that has an average number of moles of ethylene oxide units per mole of triglyceride molecules of 10 to 45 and wherein the solvent is either xylene or mixtures of xylene with methyl isobutyl ketone;
    wherein the solvent comprises 0-10% water, by weight, based on the weight of the solvent; and
    wherein the combination of (a), (b), and (c) in the solvent borne coating composition forms dispersed particles and the dispersed particles have a particle size of less than 50 micrometers.

2. The composition of claim 1 wherein said ethoxylated triglyceride has average number of moles of ethylene oxide units per mole of triglyceride molecules of 38 to 42.

3. The composition of claim 1 wherein the amount of said ethoxylated triglyceride is 0.2% to 5% based on the weight of said composition.

4. A method of providing a surface that resists marine fouling, wherein said method comprises applying a layer of the composition of claim 1 to a substrate and drying said layer or allowing said layer to dry.

* * * * *